United States Patent [19]
Boiarski et al.

[11] Patent Number: 5,173,747
[45] Date of Patent: Dec. 22, 1992

[54] INTEGRATED OPTICAL DIRECTIONAL-COUPLING REFRACTOMETER APPARATUS

[75] Inventors: Anthony A. Boiarski, Columbus; Richard W. Ridgway, Westerville, both of Ohio

[73] Assignee: Battelle Memorial Institute, Columbus, Ohio

[21] Appl. No.: 585,438

[22] Filed: Sep. 20, 1990

[51] Int. Cl.$^5$ ............................................. G01B 9/02
[52] U.S. Cl. ..................................... 356/361; 356/345; 356/128; 385/12
[58] Field of Search ............... 356/345, 361, 128, 133, 356/136, 246, 351; 250/227.17, 227.19, 227.27; 350/96.12, 96.15; 385/12, 14

[56] References Cited

U.S. PATENT DOCUMENTS

| | | | |
|---|---|---|---|
| 4,815,843 | 3/1989 | Tiefenthalga et al. | 356/128 |
| 4,950,074 | 8/1990 | Fabricius et al. | 356/133 |
| 4,989,979 | 2/1991 | Buckman | 356/345 |

FOREIGN PATENT DOCUMENTS 0108527  5/1984  European Pat. Off. ............ 356/246

*Primary Examiner*—Samuel A. Turner
*Attorney, Agent, or Firm*—Philip M. Dunson; Klaus H. Wiesmann

[57] ABSTRACT

In apparatus useful in immunoassay of a fluid, light is directed to an optical sensor wherein the light is transmitted to a replaceable optical device that is responsive to index of refraction in a sensing region thereof that is exposed to the fluid. One portion of the light is transmitted via a reference path to a first detector. Another portion of the light is transmitted via a sensing path that includes the sensing region to another detector. A ratioing device receives an output from each detector and provides a signal responsive to the ratio of the outputs. The replaceable optical device typically comprises a pair of channel waveguides in directional coupling arrangement, or a pair of channel waveguides in an interferometer arrangement, or a ridge waveguide having a serpentine path.

11 Claims, 6 Drawing Sheets

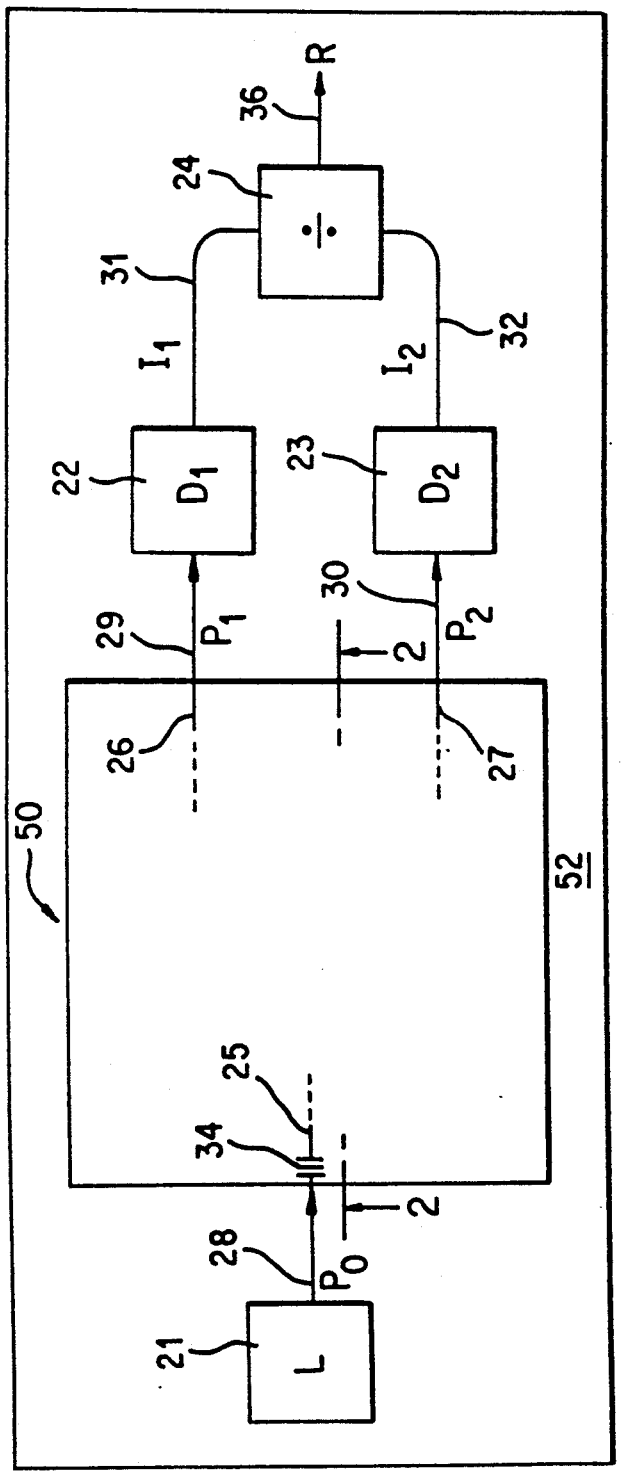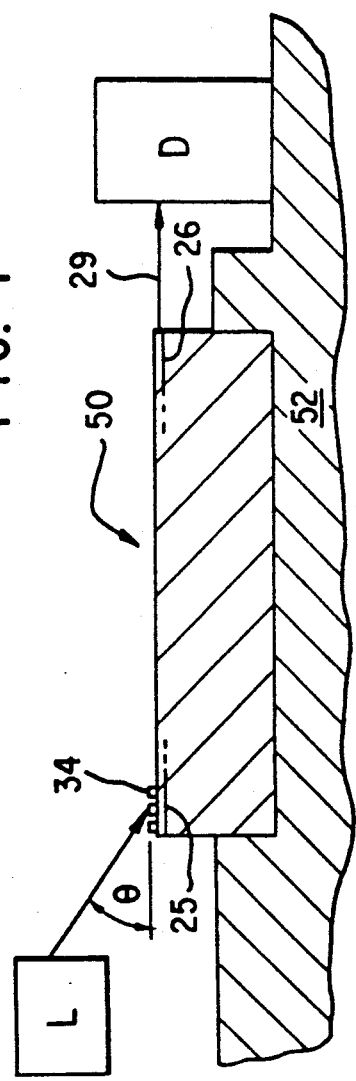

INTEGRATED OPTICAL DIRECTIONAL-COUPLING REFRACTOMETER APPARATUS

FIELD this invention relates to methods and apparatus useful in immunoassay of a fluid. In typical embodiments of the invention, light is directed to an optical sensor wherein the light is transmitted to a replaceable optical device that is responsive to index of refraction in a sensing region thereof that is exposed to the fluid. One portion of the light is transmitted via a reference path to a first detector. Another portion of the light is transmitted via a sensing path that includes the sensing region to another detector. A ratioing device receives an output from each detector and provides a signal responsive to the ratio of the outputs. The replaceable optical device typically comprises a pair of channel waveguides in directional coupling arrangement, or a pair of channel waveguides in an interferometer arrangement, or a ridge waveguide having a serpentine path.

Typical embodiments of the invention comprise integrated optics devices for immunoassay of whole blood or other body fluids, typically including low cost, disposable sensors in channel waveguide configurations such as serpentine multimode waveguides, single mode waveguides in coupler configurations, and single mode waveguides in interferometer configurations.

BACKGROUND

There is need for low cost, rapid, and accurate means for quantitative analysis of whole blood and other body fluids in medical diagnostics.

Some of the methods representative of the current state of the art have been recently reviewed by Bluestein, et al, [Bluestein, B. I., Walczak, I. M., and Chen, S., "Fiber Optic Evanescent Wave Immunosensors for Medial Diagnostics" Tibtech, 8, 161–168, June, 1990].

Biosensors provide rapid response, real time monitoring of the sample/sensor interaction to produce an electronically quantified result. A biomolecular component of the sensor is used to recognize the analyte of interest. These recognition components include molecules such as antibodies, enzymes, lectins, hormones, DNA, and neuro-transmitter receptors. For example, when antibodies are used to recognize the appropriate antigens, the device can be referred to as an immunosensor. Typically, the recognition or binding of antibodies and antigens is a chemical reaction with very high equilibrium association constant. The sensors are not reusable; they are used once and then discarded. Therefore, a suitable device must provide for easy replacement of the sensor portion, and the sensor must be inexpensive and easy to manufacture.

Devices for obtaining a quantitative result from the binding reaction have used techniques such as electrochemical, piezoelectric, capacitance, and optical detection schemes. One type of optical device uses surface plasmon resonance for measurement and is characterized by use of a metallic or metal-like film that interacts with the light in a manner that varies with the angle of light beam incidence. Another type of optical device, often referred to as evanescent wave type, requires the use of a fluorphor such as fluorescein and measures resultant fluorescent radiation. Such sensors typically comprise flat plates or the surface of cylindrical rods as reviewed by Bluestein, et al.

Another class of sensors, known as distal tip sensors, use optical fibers to convey light to the distal end where the reaction is monitored by reflected light form light scattering or fluorescence from fluophors.

Optical fibers have been used in devices to measure the density of protein in blood as described by Minekane in Japanese Patent 56-107419, issued Aug. 25, 1981, for a Densitometer (Application 55-9304). The fiber dipped in the sample is in the shape of a U, with the core exposed at the bent bottom. Light leaks from the exposed core depending on the concentration of protein, and the reduced light intensity that is transmitted is compared to the initial light intensity. It is well known that the leakage of light from an optical fiber depends on the radius of curvature and the index of refraction of the medium adjacent the fiber such as the cladding or the liquid sample in contact with the exposed fiber core. In such devices, which comprise a form of refractometer, the flexible unsupported fiber can have only a short length of the fiber exposed to the liquid while maintaining a fixed curvature. The limited exposed area precludes adaptation of this technique to immunoassay requiring a coating of antibodies on a significant area of the optical fiber. One typical embodiment of the present invention provides a novel way of adapting the principle of leaky fibers to planar integrated optic devices for immunoassay.

The current known technology for fabricating integrated optical devices in the form of channel waveguides is adequate for producing small optical devices by mass production techniques using photolithography and microfabrication. Such technology is applicable to typical embodiments of the present invention directed to accurate, lost-cost, replaceable sensors.

Integrated optical transducers comprising channel waveguides in the form of Mach Zehnder interferometers are known. Johnson (U.S. Pat. No. 4,515,430) discloses such an interferometer for measurement of temperature. Arms of unequal length in the interferometer utilize the temperature dependent coefficient of expansion of waveguides. Fabricius, et al (German Patent DE 381 4844, European Patent 340577) disclose an interferometer comprising a reference arm covered with substrate and an exposed measurement arm for measuring the refractive index of liquids. Means for compensating the effect of variation in source light intensity are not disclosed. The exposed waveguide arm does not contain a coating for reaction with components of the liquid sample as required for immunoassay and as in some typical embodiments of the present invention.

Another type of integrated optic device, the directional coupler, is employed in other typical embodiments of this invention. Such devices have not previously been considered for use in measurement of liquid properties or chemical reactions.

DISCLOSURE

Typical apparatus according to the present invention, useful in immunoassay of a fluid, comprises means for directing light to an input portion of optical sensing means having means for transmitting the light to replaceable optical means responsive to index of refraction in a predetermined sensing region thereof that is exposed to the fluid, means for transmitting a first predetermined portion of the light via a reference path to first detecting means, means for transmitting a second predetermined portion of the light via a sensing path that includes the predetermined sensing region to second detecting means, and means for receiving an output form each detecting means and providing a signal responsive to the ratio of the outputs.

In some typical embodiments of the invention, the replaceable optical means comprises a plurality of channel waveguide means in directional coupling arrangement. Typically the channel waveguide means are adjacent and substantially parallel over a predetermined region, one of them being in the reference path and another being in the sensing region of the sensing path, and the waveguide means in the sensing region typically comprises a coating that can react with the fluid.

In other typical embodiments of the invention, the replaceable optical means comprises a plurality of channel waveguide means in an interferometer arrangement. Typically an arm of the interferometer passes through the sensing region, and that arm typically comprises a coating that can react with the fluid.

In still other embodiments of the invention, the replaceable optical means comprises ridge waveguide means having a serpentine path that passes through the sensing region, and in the sensing region typically comprises a coating that can react with the fluid. In such embodiments the light transmitting means in the reference path typically also comprises ridge waveguide means having a serpentine path.

DRAWINGS

FIG. 1 is a schematic plan view representation of typical apparatus according to this invention with a replaceable planar integrated optic sensor.

FIG. 2 is a schematic cross sectional view, taken in the plane 2—2, of a portion of the apparatus in FIG. 1.

CARRYING OUT THE INVENTION

This invention comprises methods and apparatus for obtaining an immunoassay of whole blood or other body fluids by attaching antibodies or antigens to the surface of an optical waveguide. The reaction of antibodies and antigens produces a change in the refractive index of the coating at the surface of the waveguide that can affect a property of the light in the waveguide that can be measured to monitor the immunoassay reaction. The property of the light affected by the reaction typically can be a relative change in light intensity between two coupled waveguides, or a change in the phase of light in one arm of an interferometer, or a diminution of light intensity as in a leaky waveguide.

Figure 3:
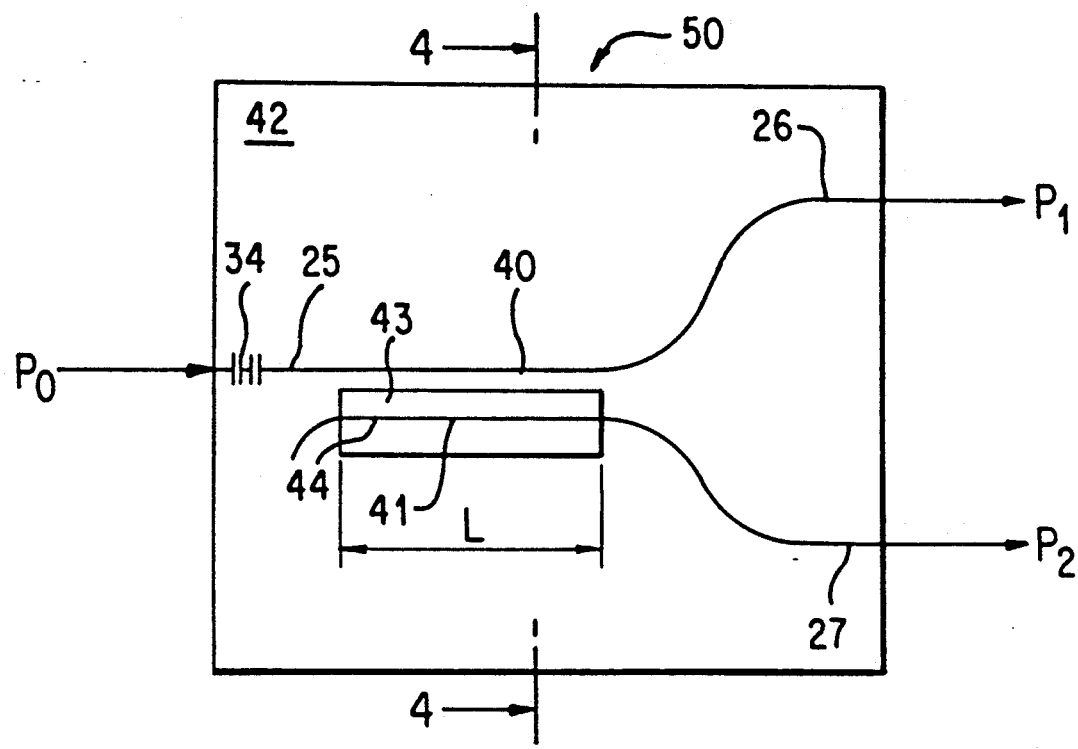
FIG. 3 is a schematic plan view of a typical planar sensor with optical waveguides in a directional coupler arrangement as included in some typical embodiments of the invention.
Figure 8:
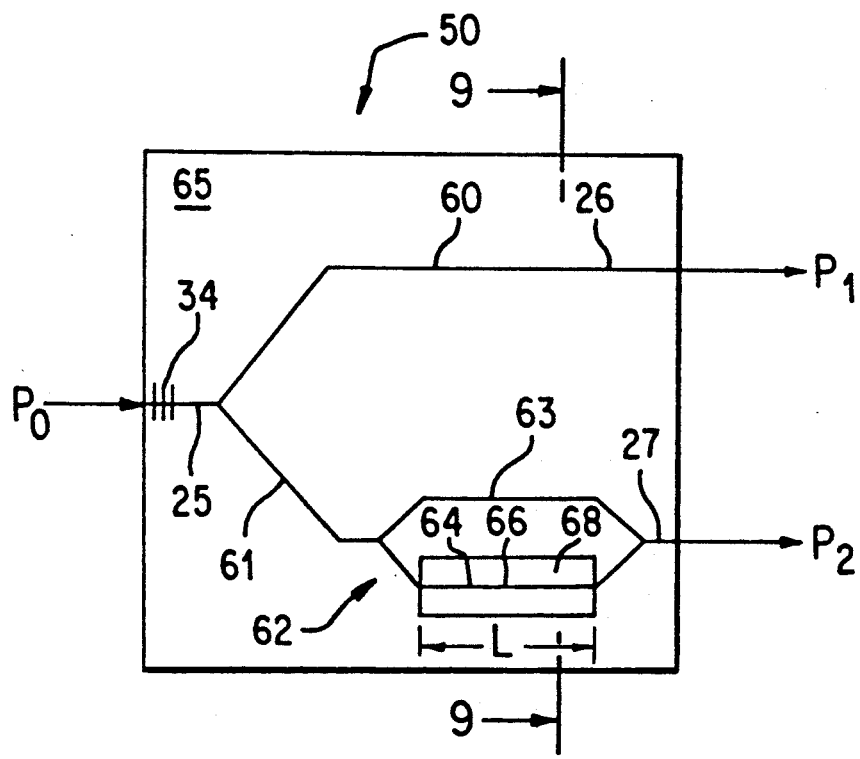
FIG. 8 is a schematic plan view of a typical planar sensor with optical waveguides in an interferometer arrangement as included in some typical embodiments of the invention.
Figure 10:
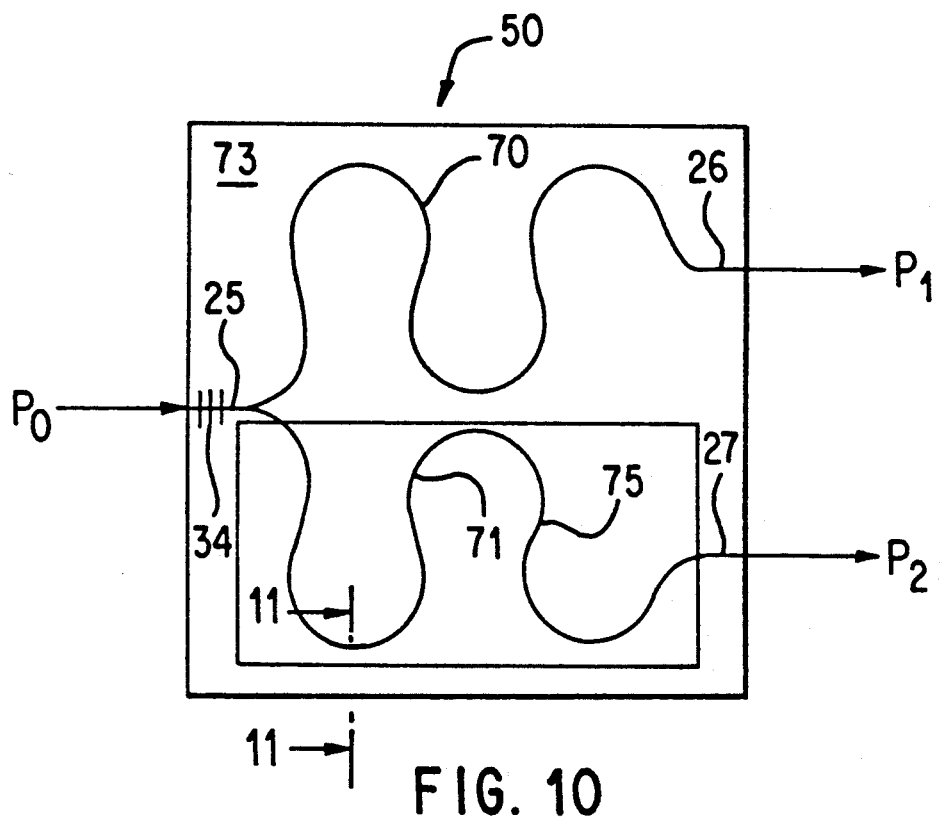
FIG. 10 is a schematic plan view of a typical planar sensor with optical waveguides in a serpentine arrangement as included in some typical embodiments of the invention.

Apparatus according to this invention shown schematically in FIGS. 1 and 2 comprises a light source 21, a first detector 22, a second detector 23, a ratio device 24, and a replaceable planar sensor 50 positioned in a recess in a baseplate 52, with a snug fit. The planar sensor 50 comprises waveguides arranged in accordance with various embodiments of this invention as shown in FIGS. 3, 8, and 10. Light from light source 21 is coupled into an entry waveguide 25 and uncoupled from exit waveguides 26, 27. Typically, the light source 21 can be a laser diode producing a monochromatic coherent light beam 28 of intensity $P_o$ that is coupled into the entry waveguide 25 by use of grating 34 with light 28 incident on the grating 34 at an angle $\theta$ shown in FIG. 2. A reference light signal 29 of intensity $P_1$ emerging from exit waveguide 26 is directed at the first detector 22 to produce a reference electrical signal 31 of value $I_1$. Similarly, a measurement light signal 30 of intensity $P_2$ is directed to the second detector 23 to produce an electrical 32 of value $I_2$. Electrical signals 31, 32 are combined in the ratio device 24 to produce a ratio signal 36 of value R, where $R=I_1/I_2$.

The use of a grating 34 to introduce light into the entry waveguide 25 is preferred especially for signal mode channel waveguides. However, end coupling can be used. Also, gratings can be used to decouple light from exit waveguides 26, 27 to detectors 22, 23 respectively.

The reference light signal intensity $P_1$ is used to compensate for variations in the intensity of the light source 21 and inefficiency of coupling light into the entry waveguide 25. Additionally, the measurement light signal intensity $P_2$ is influenced by the index of refraction changes in the sensor region caused by the fluid sample.

Figure 4:
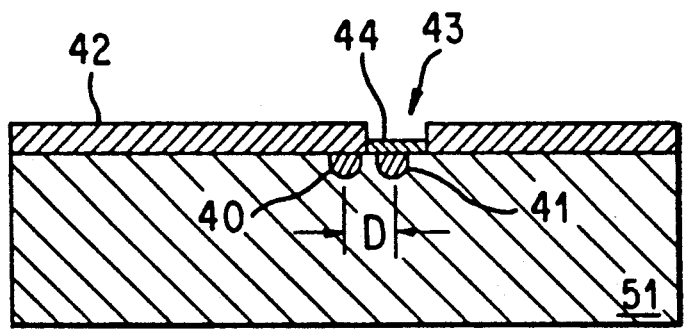
FIG. 4 is a schematic cross sectional view, taken in the plane 4—4, of a portion of the sensor in FIG. 3.

In one typical embodiment of the present invention shown in FIGS. 3 and 4, the sensor comprises integrated optic channel waveguides in the form of a directional coupler. Waveguides 40, 41 are formed on a planar substrate 51 such as lithium niobate by indiffusion of a material such as titanium using well-known techniques of photolithography for microfabrication of integrated optical circuits. Coherent light form a light source, such as a laser diode, is coupled into one end of a first waveguide. The preferred method of coupling light into a single mode waveguide is to use a grating, although a prism or end coupling can be used. Gratings are used to couple light into one end of the first waveguide 40. Light uncoupled from the opposite end of the first waveguide and from the adjacent end of the second waveguide is directed to a first detector 22 and a second detector 23 respectively. The electrical signals 31, 32 from the detectors are combined in a ratio device 24 to produce an output signal 36 ($R=I_1/I_2$).

The integrated optic directional coupler shown in FIGS. 3 and 4 comprises two optical waveguides, portions of which are positioned close together (eg less than 5 micrometers) over an interaction length L, so that light in one waveguide evanescently couples into the other waveguide. The amount of light that couples from the first waveguide 40 to the second waveguide 41 (or vice versa) depends on the length of the interaction region L, the distance between the waveguides D, and the effective index of refraction of the two waveguides. The latter depends on the geometrical parameters of each waveguide and the material surrounding each waveguide including the superstrate.

The first waveguide 40 is covered by a first superstrate 42 of known and constant index of refraction. A portion of the second waveguide 41 is uncovered over an interaction length L. For immunoassay, the uncovered surface of the second waveguide 41 is coated with antibodies which constitutes a second superstrate 44. By suitable choice of material for the first superstrate relative to the superstrate of antibody coating on the second waveguide, the effective index of the waveguides are closely matched or in synchronism.

To prepare the sensor 50 for use, the uncovered region 43 is exposed to an appropriate solution to deposit a layer of antibody coating 44 on the exposed portion of the waveguide 41. The sensor is then rinsed and dried. The coated sensor can be stored in protective packaging for future use.

When a sample containing antigens is added to the cavity 43 above the second waveguide 41 coated with antibodies 44 a binding reaction of antigens to antibodies occurs which changes the index of the coating 44 relative to the first superstrate 42. This changes the amount of coupling of light which affects the relative intensity of light $P_1$, $P_2$ emerging from each waveguide as measured by detectors and reflected in the value of the ratio R. A change in the value of R can be correlated with the concentration of antigens in the sample.

The operation of the sensor can be better understood by some quantitative examples based on the theory of operation of directional couplers. In many cases the coupler can be described in terms of only two fundamental parameters, an asynchronism parameter, $\delta$, which is essentially the difference in mode index between the two waveguides, and the coupling coefficient, K, which depends primarily on the waveguide separation. Often the half-beat length $L_c$, defined by $L_c = \pi/2K$, is used as a parameter instead of K. The half-beat length is the interaction length at which all light transfers from one waveguide to the other. At an interaction length equal to a full beat length $2L_c$ all of the light will transfer from one waveguide to the other and then back to the first waveguide.

When the mode indices of the two waveguides are equal ($\delta=0$) the two waveguides are in synchronism and the highest coupling occurs. Under this condition the phase velocities within each waveguide are equal so that light coupling over from waveguide 1 to waveguide 2 will be in phase with light already in waveguide 2 resulting in constructive interference. Furthermore, coupled light in waveguide 2 that couples back to waveguide 1 is 180 degrees out of phase with light already in waveguide 1, resulting in destructive interference. If the two waveguides are not synchronous ($\delta \neq 0$) then the velocities are not equal and the light does not couple as efficiently.

For a directional coupler of length L, the amount of light that couples from waveguide 1 to waveguide 2 is given by $$P_2 = P_{in} \frac{\sin^2 \kappa L \Psi}{\Psi}$$

where $P_{in}$ is the input optical intensity, $$\Psi = (1 + \delta^2/K^2)^{\frac{1}{2}}$$

$$\delta = \frac{\pi}{\lambda}(n_1 - n_2)$$

$\lambda$ is the optical wavelength, and $n_1$ and $n_2$ are the mode indices in waveguide 1 and waveguide 2 respectively. Assuming lossless waveguides, the amount of light remaining in the first waveguide is given by $$P_1 = P_{in} - P_2$$

Figure 5:
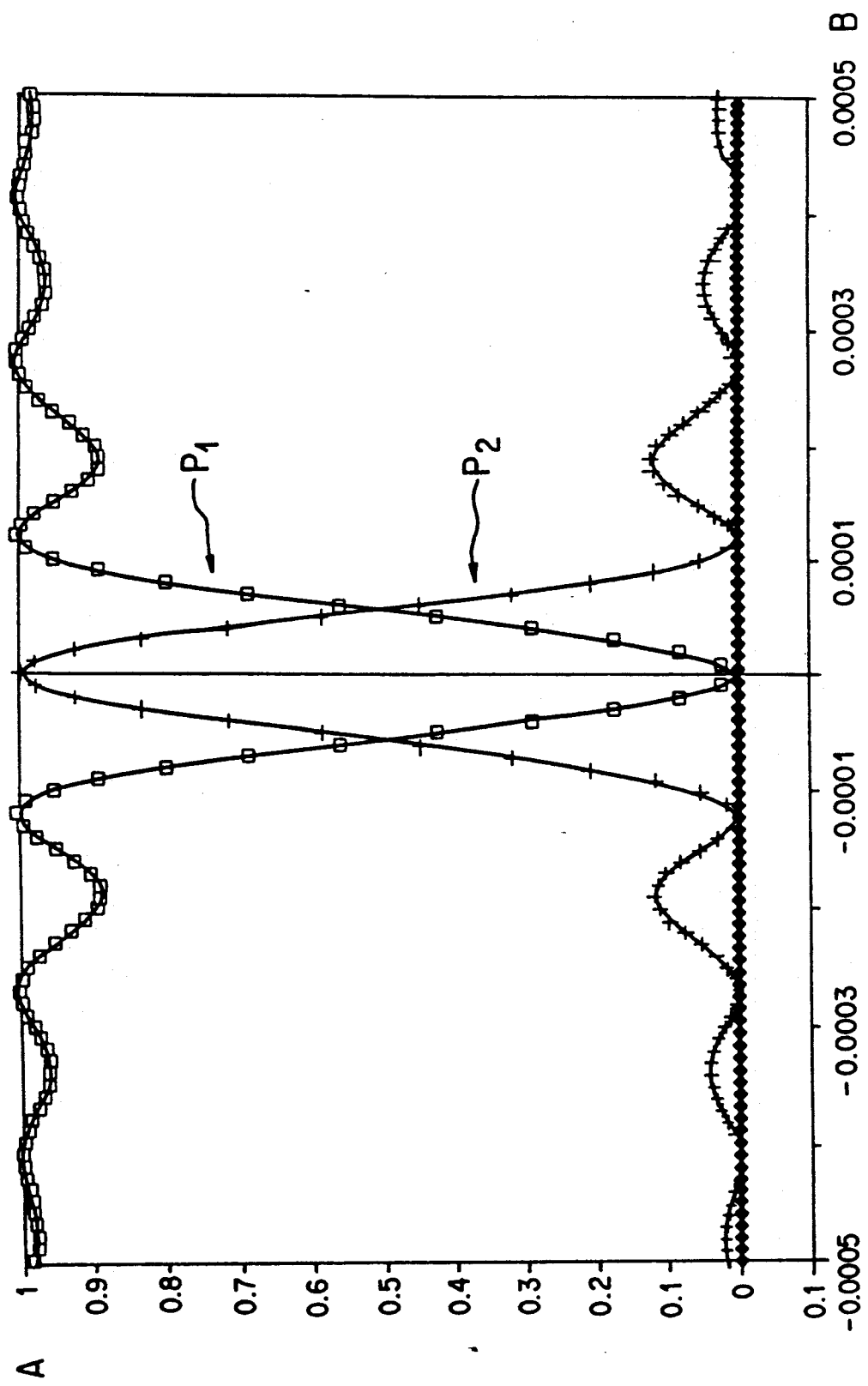
FIG. 5 is a graph showing the calculated relative output light intensity in coupled waveguides as in FIGS. 3 and 4, as a function of effective refractive index differential.

FIG. 5 shows the output signals $P_1$ and $P_2$, as a function of the difference in mode index. In this figure, the following values of the parameters are assumed
$n_1 = 1.5$
$n_2 = 1.5$
$K = 260$ m$^{-1}$
$L = 6$ mm
$\lambda = 840$ nm For this example an index change of 0.0001 causes the output signals $P_1$ and $P_2$ to completely switch (with $\Delta n = 0$, all light exists $P_1$; with $\Delta n = \pm 0.0001$ all light exits $P_2$). It is estimated that index changes of $10^{-6}$ can be sensed with relatively simple circuitry. In general, increasing the interaction length L will increase the sensitivity, and increasing the coupling coefficient, K, by placing the waveguides closer together, will make the sensor less sensitive to changes in index.

Figure 6:
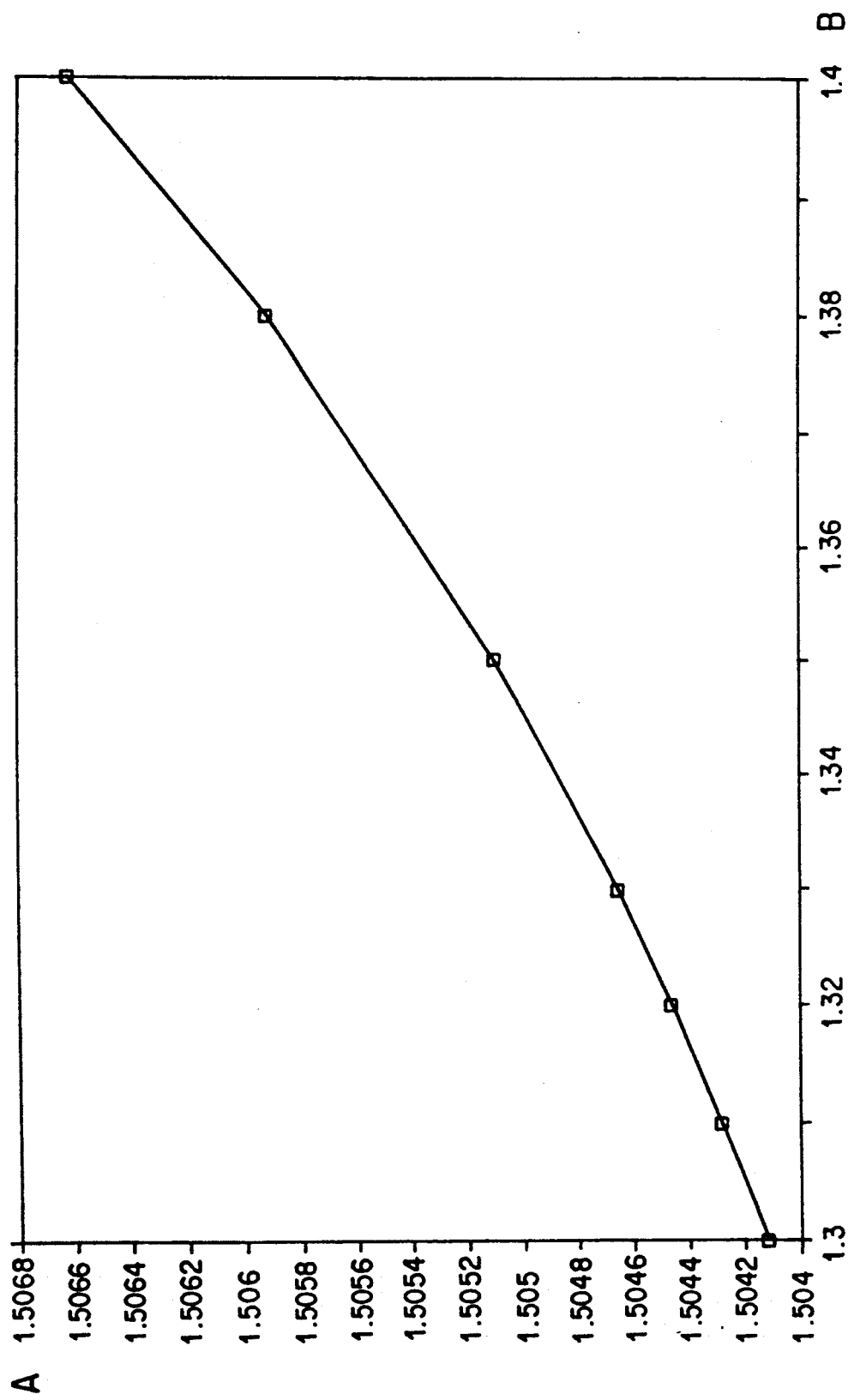
FIG. 6 is a calculated curve of effective refractive index of a waveguide versus index of refraction of the contiguous superstrate.

The relationship between the index of the superstrate and the mode index in the measurement waveguide 41 can be estimated by solving for the boundary conditions in a single-mode slab waveguide (Ref. *Integrated Optical Circuits and Components*, Edited by Lynn Hutcheson, Mercel Dekker, Inc., New York, pp. 11–25, 1987). FIG. 6 shows an example of how the index of the superstrate affects the mode index in the waveguide. For this example, the waveguide was 0.5 micrometers thick with a material index of 1.5. For the values of the parameters assumed in FIG. 6, changes in the superstrate index in the second decimal place affect the mode index in the fourth decimal place. Using FIG. 5 and FIG. 6, it is estimated that an integrated optical directional coupler biosensor can measure superstrate index changes in the fourth decimal place (since the directional coupler can measure mode indices to the sixth decimal place).

As shown in FIG. 5 a mode index change of 0.0001 would cause light to completely transfer from one waveguide to the other waveguide. From the slope of the curve in FIG. 6 a mode index change of 0.0001 corresponds to a superstrate index change of about 0.0006 units at an index of 1.33 and about 0.0035 units at an index of 1.39

There are several modes of operation. If the sensor is prepared with a superstrate index $n_2$ on the antibody coated waveguide 41 equal to the superstrate index $n_1$ on the reference-intensity waveguide 40, all of the light will be transferred from the waveguide 40 to the waveguide 41 in the half-beat interaction length. After the sample is added, the antigen/antibody binding reaction occurs, increasing $n_2$ relative to $n_1$; $\Delta n$ will become negative and light will transfer back to the waveguide 40 and the ratio R will increase. Using FIG. 5 as an example, the reaction can be monitored over an effective index change of 0.0001. Alternatively, the useable range of index change can be doubled if the sensor is prepared such that superstrate index $n_1$ is greater than superstrate index $n_2$ by more than an index of difference of 0.0001. All of the light will remain in the waveguide 40 initially. After the sample is added and the reaction proceeds increasing $n_1$, the effective index will decrease. The reaction can be monitored from an index of difference of $+0.0001$ to $-0.0001$ (right to left in FIG. 5) as the light transfers from the waveguide 40 to the waveguide 41 and back to the waveguide 40.

Figure 7:
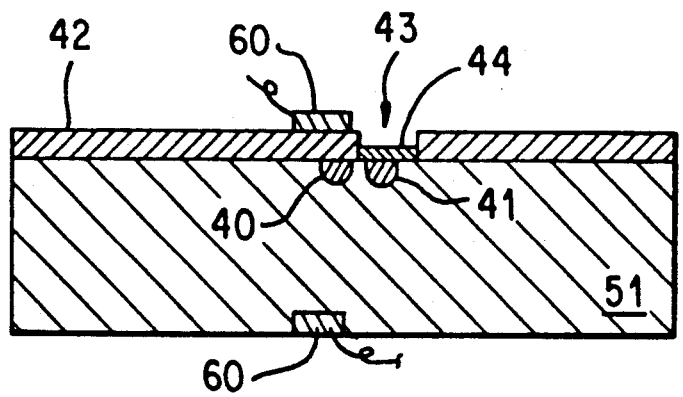
FIG. 7 is a schematic cross sectional view of a directional coupler with electrodes for modifying the mode index electrooptically as included in some typical embodiments of the invention.

The above device can be modified to allow preadjustment of the effective index of the reference-intensity waveguide 40. As shown in FIG. 7 metal electrodes are provided above and below the waveguide 40 and connected to a source of voltage (not shown) so that the effective index of the waveguide 40 can be adjusted by the electrooptic effect. For example, the effective index of the reference waveguide can be fine tuned electrooptically such that $\Delta n = 0$ initially if desired. Alternatively, after the reaction at waveguide 2 has proceeded to change the index difference from $+0.0001$ to $-0.0001$ the index of the reference-intensity waveguide 40 can be increased electrooptically to repeat the monitoring. This method would increase range of reaction change in index that can be monitored.

Figure 9:
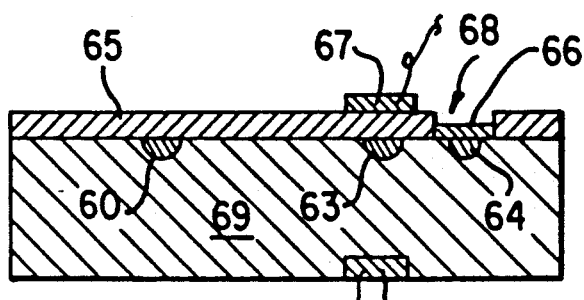
FIG. 9 is a schematic cross sectional view, taken in the plane 9—9, of the sensor in FIG. 8 with the addition of electrodes for modifying the mode index electrooptically.

In another embodiment of the present invention shown in FIGS. 8 and 9, the sensor comprises integrated optic channel waveguides in the form of a Mach-Zehnder interferometer. Single-mode channel waveguides are formed on a planar substrate 69 such as lithium niobate by indiffusion of a material such as titanium using well-known techniques of photolithography for microfabrication of integrated optical circuits. Light from a coherent light source 21, such as a laser diode, is coupled into the entry waveguide 25. The preferred method of coupling light into the single mode waveguide is to use a grating 34, although a prism or end coupling might be used. Light in the entry waveguide is split into two branches 60, 61, one of which comprises a reference-intensity waveguide 60 to provide a reference signal $P_1$ to compensate for variations in the intensity of the light source and in the efficiency of coupling. Light in the other branch 61 travels through the interferometer 62 which comprises two arms 63, 64 of equal length to minimize the effect of temperature. One arm 63 is the reference-phase waveguide arm, which is covered by a protective layer 65 of known index of refraction. The other, active, arm 64 is exposed.

The active waveguide arm 64 is coated with antibodies for immunoassay. When a sample containing antigens to be measured is added to the cavity 68 above the active arm, antigens bind to the antibodies, and the mode index of the active arm waveguide 64 is changed, resulting in a phase change relative to the reference-phase waveguide arm 63. The result is a variation in intensity of the light $P_2$ from the interferometer due to the constructive or destructive interference depending on the phase difference of the light in each arm of he interferometer. The intensity change $P_2$ is measured by the detector 23. The electrical signal $I_2$ from the second detector 23 is compared to the electrical signal $I_1$ from the first detector 22 in a ratio device 24 ($R = I_1/I_2$). A change in the value of the ratio R is indicative of a reaction of antigens binding to antibodies on the active coated arm. The rate of change of the ratio R can be correlated with the concentration of antigens in the sample.

The sensor is very sensitive to changes in the mode index. For example, for a length of active arm of $L=5$ millimeters and a light source wavelength of $\lambda = 0.633$ micrometer, there is a phase change of $\pi/2$ for a mode index change of $3 \times 10^{-5}$. The phase changes over large changes in mode index produces a repetitive sine wave of light intensity $P_2$ from the interferometer with similar effect on the detector signal ($I_2$) and ratio (R). Thus, suitable electronic circuitry can include a cycle counter (not shown) to monitor the antibody/antigen reaction over a large change in mode index. For some applications, the counter can be used to measure cycles per unit time which can be correlated with reaction rate and the concentration of antigens in the sample.

As shown in FIG. 9, electrodes 67 can be placed adjacent the reference-phase waveguide 63 to adjust the effective mode index of the waveguide by the electrooptic effect.

Figure 11:
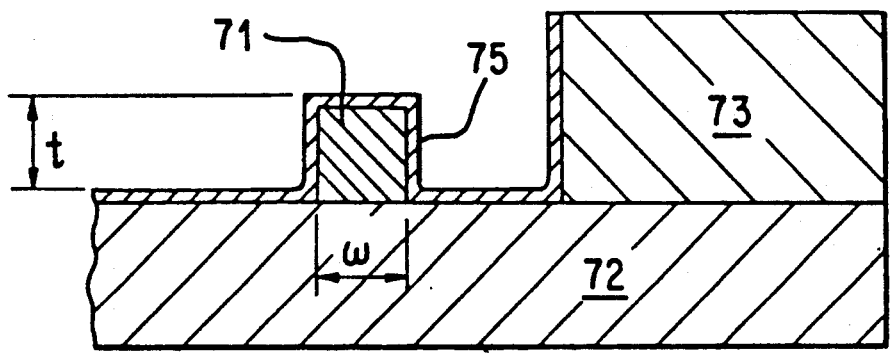
FIG. 11 is an enlarged schematic cross sectional view, taken in the plane 11—11, of a portion of the planar sensor in FIG. 10.

In another embodiment of the invention, shown in FIGS. 10 and 11, the planar sensor 50 comprises multimode ridge waveguides 70, 71 formed on a planar substrate 72 in a serpentine arrangement. A waveguide material of higher index of refraction ($n_1$) is coated on the substrate and the serpentine waveguide is formed by photolithography involving masking and etching. The resulting serpentine arrangement of ridge waveguides is upraised from the substrate to a thickness (t) that is typically 100 to 150 micrometers. The cross section of the waveguide can be square, rectangular, or hemispherical. Typically, the width (w) of the waveguide is 100 to 150 micrometers.

Typically, the light source is monochromatic, such as a laser diode or light-emitting-diode, and light 28 is coupled into the entry waveguide 25 with a grating 34. Alternatively, the thickness and width of the waveguide are sufficient to support multimode light and facilitate end coupling of the light into the entry waveguide. The intensity of light $P_2$ emerging from the other end of the serpentine waveguide 71 is measured with a first detector 23. The signal from the first detector 23 is compared to the signal from a second reference-intensity detector 22 that measures the effective intensity $P_1$ of the light leaving the serpentine reference-intensity waveguide 70. The use of a second reference detector provides compensation for the intensity variation in the light source and any inefficiency of coupling of light into the entry waveguide 25. The reference-intensity serpentine waveguide 70 is provided with a protective coating 73 of refractive index $n_3$ lower than the waveguide index $n_1$. To prepare the sensor for use, the unprotected region is contacted with an appropriate solution to deposit a layer of antibody coating 75 on the measurement waveguide 71. The sensor is then rinsed and dried. The coated sensor can be stored in protective packaging for future use.

The antibody coating on the sides of the waveguide 71 is most effective for measurement. For example, for a waveguide of square or rectangular cross section as in FIG. 11, the effective area of coating is the product of twice the thickness (i.e. 2t) times the length of the serpentine waveguide.

For an immunoassay, the sensor is exposed to a solution (eg blood) containing antigens to be measured. Those antigens reacting with the antibodies coated on the effective area of the waveguide will change the refractive index of the coating (usually an increase in index). The change in refractive index of the coating is a measure of the concentration of antigens present in the sample. The change in refractive index of the coating results in a change in intensity of light $P_2$ in the serpentine waveguide 71 which is measured at the detector 23.

A portion of the input light exclusive of that in the reference-intensity waveguide 70) enters the serpentine measurement waveguide 71 and negotiates the various bends as shown in FIG. 10. At each bend, a certain amount of light is lost depending on the index difference ($\Delta n$) between the waveguide 71 (index $n_1$) and the coating 75 (index $n_2$) where $$\Delta n = n_1 - n_2 > 0$$

The smaller the value of $\Delta n$, the more light is lost. Thus, the intensity of light $P_2$ exiting the serpentine waveguide 71 and detected by the detector will be proportional to $\Delta n$. The intensity of the light $P_1$ exiting the protected reference-intensity serpentine waveguide 70 is not affected by the reaction at the other waveguide 71. As previously described relative to FIG. 1, the ratio ($R = I_1/I_2$) is used to monitor the progress of the reaction. An initial ratio ($R_o$) is determined for the sensor when the sample is first added. As the reaction proceeds by bonding of the antigens to antibodies, the index of the coating ($n_2$) changes (typically increases) to a final value when all of the antigens are bonded or all the antibody sites have been used. As the bonding reaction proceeds, $n_2$ increases, $\Delta n$ decreases, $I_2$ decreases, and the ratio $I_1/I_2$ increases. An increase in the ratio (R) indicates the presence of antigens in the sample and the rate or change of R with time is proportional to the concentration of antigens in the sample. The change in the ratio R with time can be plotted on an x-y recorder or suitable electronics can be provided to measure and display the rate of change of ratio R with time. By suitable calibration, the display can read directly in concentration of antigen.

The sensitivity of the sensor is proportional to the length of the serpentine waveguide 71, the number of bends, and the radius of the bends. The serpentine waveguide can take several forms to maximize the length in a given area.

The planar sensor with serpentine ridge waveguides can have several arrangements with regard to the radius of curvature and number of bends. The symmetrical pattern of the reference-intensity waveguide and the measurement waveguide provides for equal length, to minimize the effect of temperature. However, the reference-intensity waveguide need not be in a serpentine arrangement since there is no need for bends to accentuate loss of light. The function of the reference-intensity waveguide is to compensate for variations in light source intensity and efficiency of light coupling into the entry waveguide. Thus, the reference-intensity waveguide can be straight across the planar sensor similar to the reference-intensity waveguide 60 of the interferometer embodiment of FIG. 8. Alternatively, the reference-intensity waveguide may be arranged as a loop with exit waveguide on the same side of the planar sensor as the entry waveguide. The measurement waveguide 71 needs to be serpentine or have at least some minimum amount of curvature. In an alternative arrangement, the serpentine measurement waveguide can loop back such that the exit waveguide was on the same side of the planar sensor as the entry waveguide.

The apparatus in several embodiments has been described as typically used with an antibody coating to measure antigens in the sample, However, the sensor can be coated with antigens to measure antibodies in the sample. The coating can be other molecules to detect enzymes, lectins, hormones, DNA, and neuro-transmitters. Typically, the measurement waveguide is provided with a coating that changes its index of refraction by reaction with components of the sample. However, the devices of this invention can be used with an uncoated measurement waveguide to measure the change in refractive index of a sample relative to some reference such as water.

The Appendix to the application leading to this patent, comprising 15 pages, and present in the file of this patent, brings out further details of typical embodiments, as well as related drawings, graphs, tables, and other explanations that may be of interest in connection with the present invention.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit or scope of the invention.

We claim:

1. Apparatus useful in immunoassay of a fluid, comprising:
   means for directing light to an input portion of optical sensing means having,
   means for transmitting the light to replaceable optical means, wherein the replaceable optical means comprises a plurality of channel waveguide means in directional coupling arrangement responsive to index of refraction in a predetermined sensing region thereof that is exposed to the fluid,
   means for transmitting a first predetermined portion of the light via a reference path to first detecting means,
   means for transmitting a second predetermined portion of the light via a sensing path that includes the predetermined sensing region to second detecting means, and
   means for receiving an output from each detecting means and providing a signal responsive to the ratio of the outputs.

2. Apparatus as in claim 1, wherein the channel waveguide means are adjacent and substantially parallel over a predetermined region, one of them being in the reference path and another being in the sensing region of the sensing path.

3. Apparatus as in claim 2, wherein the waveguide means in the sensing region comprises a superstrate that can react with the fluid.

4. Apparatus as in claim 3, wherein the superstrate comprises antigen or antibody, having an index of refraction that changes in response to a binding reaction of antibody or antigen.

5. Apparatus useful in immunoassay of a fluid, comprising:

a substrate with an optical directional coupler integrated therein having, a first optical waveguide with a first end for receiving or exiting light and a second end for receiving or exiting light, a second optical waveguide with an end for receiving or exiting light, the first and second optical waveguides having portions which are positioned close together over an interaction region, so that light in the first waveguide evanescently couples into the second waveguide or vice versa, and a first superstrate of known and constant index of refraction covering the first optical waveguide, and covering the second waveguide except for an interaction length L.

6. Apparatus as in claim 5, wherein the interaction length L is covered by a second superstrate that can react with the fluid.

7. Apparatus as in claim 6, wherein the second superstrate comprises antigen or antibody, having an index of refraction that changes in response to a binding reaction of antibody or antigen.

8. Apparatus as in claim 5, comprising:

a first superstrate that provides a close match of the index of refraction relative to the second superstrate.

9. Apparatus as in claim 5, wherein the mode indices of the waveguides are about equal 10. Apparatus as in claim 5, comprising means for preadjusting the effective index of the first waveguide.

11. Apparatus as in claim 10, wherein the means for preadjusting the effective index of the first waveguide comprises:

a first metal electrode above the first waveguide in the vicinity of the interaction region, and a second metal electrode below the first waveguide in the vicinity of the interaction region.

* * * * *